(12) United States Patent
Sharma

(10) Patent No.: US 11,278,545 B2
(45) Date of Patent: *Mar. 22, 2022

(54) OPTICAL CORRECTION

(71) Applicant: PRESBYOPIA TREATMENTS LIMITED, Caterham (GB)

(72) Inventor: Anant Sharma, Bedford (GB)

(73) Assignee: PRESBYOPIA TREATMENTS LIMITED, Caterham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/489,950

(22) Filed: Apr. 18, 2017

(65) Prior Publication Data

US 2017/0216281 A1     Aug. 3, 2017

Related U.S. Application Data

(60) Division of application No. 14/479,852, filed on Sep. 8, 2014, now Pat. No. 9,623,007, which is a division of application No. 13/692,257, filed on Dec. 3, 2012, now Pat. No. 8,829,037, which is a continuation of application No. 12/334,916, filed on Dec. 15, 2008, now abandoned.

(30) Foreign Application Priority Data

Dec. 15, 2007   (GB) ..................................... 0724558

(51) Int. Cl.

| | | |
|---|---|---|
| *A61K 31/4178* | (2006.01) | |
| *A61K 31/496* | (2006.01) | |
| *A61P 27/02* | (2006.01) | |
| *A61P 27/10* | (2006.01) | |
| *A61K 31/138* | (2006.01) | |
| *A61K 31/385* | (2006.01) | |
| *A61K 31/4168* | (2006.01) | |
| *A61K 31/498* | (2006.01) | |
| *A61K 31/222* | (2006.01) | |
| *A61K 9/00* | (2006.01) | |
| *A61K 31/216* | (2006.01) | |

(52) U.S. Cl.
CPC .......... *A61K 31/496* (2013.01); *A61K 9/0048* (2013.01); *A61K 31/138* (2013.01); *A61K 31/216* (2013.01); *A61K 31/222* (2013.01); *A61K 31/385* (2013.01); *A61K 31/4168* (2013.01); *A61K 31/4178* (2013.01); *A61K 31/498* (2013.01); *A61P 27/02* (2018.01); *A61P 27/10* (2018.01); *Y10S 514/912* (2013.01)

(58) Field of Classification Search
None
See application file for complete search history.

(56) References Cited

U.S. PATENT DOCUMENTS

| | | | |
|---|---|---|---|
| 3,883,225 A | 5/1975 | Rehm | |
| 4,136,177 A | 1/1979 | Lin et al. | |
| 5,360,801 A | 11/1994 | Laties et al. | |
| 5,488,050 A | 1/1996 | Neufeld | |
| 6,268,359 B1 | 7/2001 | Ogawa et al. | |
| 6,277,855 B1 * | 8/2001 | Yerxa ..................... | A61K 31/44 514/256 |
| 6,291,466 B1 | 9/2001 | Gwon et al. | |
| 6,410,544 B1 | 6/2002 | Gwon et al. | |
| 8,829,037 B2 * | 9/2014 | Sharma ................ | A61K 31/138 514/397 |
| 9,623,007 B2 | 4/2017 | Sharma | |
| 2004/0116524 A1 | 6/2004 | Cohen et al. | |
| 2005/0130906 A1 | 6/2005 | Matier et al. | |
| 2006/0177430 A1 | 8/2006 | Bhushan et al. | |
| 2006/0212007 A1 | 9/2006 | Peters et al. | |
| 2006/0257452 A1 | 11/2006 | Hughes et al. | |
| 2007/0122450 A1 * | 5/2007 | Osio Sancho ......... | G02C 7/047 424/428 |
| 2010/0298335 A1 | 11/2010 | Kaufman | |
| 2011/0152274 A1 | 6/2011 | Kaufman | |

FOREIGN PATENT DOCUMENTS

| | | |
|---|---|---|
| WO | 2008075149 A2 | 6/2008 |
| WO | 2008083118 A1 | 7/2008 |
| WO | 2010135731 A1 | 11/2010 |

OTHER PUBLICATIONS

Www.lowvisiononline.unimelb.edu, University of Melbourne, Refractive Error, Sep. 3, 2004, printed from https://web.archive.org/web/20040903163620/http://www.lowvisiononline.unimelb.edu.au:80/Screening/refractive.htm, 2 pages (Year: 2004).*
Erenmemisoglu et al., Has nicotine a local anaesthetic action?, J Basic Clin Physiol Pharmacol. Apr.-Jun. 1994;5(2):125-31., printed from https://www.ncbi.nlm.nih.gov/pubmed/8736044, 1 page, abstract only.*
Hamilton et al., Steroid-induced glaucoma after laser in situ keratomileusis associated with interface fluid., Ophthalmology. Apr. 2002;109(4):659-65.*
Krause et al., Comparative studies of pilocarpine gel and pilocarpine eyedrops, Klin Monbl Augenheilkd. Sep. 1985;187(3):178-83., printed from https://www.ncbi.nlm.nih.gov/pubmed/4068582, 1 page, Abstract only.*
Asano et al., Relationship between astigmatism and aging in middle-aged and elderly Japanese, Jpn J Ophthalmol Mar.-Apr. 2005;49(2):127-33, printed from https://pubmed.ncbi.nlm.nih.gov/15838729/, Abstract only.*
Leipert et al., Pattern electroretinogram: effects of miosis, accommodation, and defocus, Doc Ophthalmol. Dec. 1987;67(4):335-46, printed from http://www.ncbi.nlm.nih.gov/pubmed/?term=Pattern+electroretinogram%3A+Eff-ects+-of+miosis%2C+accommodation%2C+and+defocus, 1 page, abstract only.
Charman et al., Astigmatism, accommodation, and visual instrumentation, Appl Opt. Dec. 15, 1978;17(24):3903-10, printed from http://www.ncbi.nlm.nih.gov/pubmed/20208633, 1 page, Abstract only.

(Continued)

Primary Examiner — Gigi G Huang

(74) *Attorney, Agent, or Firm* — Weber Rosselli & Cannon LLP

(57) ABSTRACT

The present disclosure describes compositions which improve visual acuity and to methods for their use.

15 Claims, No Drawings

(56) References Cited

OTHER PUBLICATIONS

Tornqvist Effect of topical carbachol on the pupil and refraction in young and presbyopic monkeys (Investigative Ophthalmology, Apr. 1966,vol. 5, 2, 186-195).

Shiuey (Clin. Cardiol, vol. 19, Jan. 1996, p. 5-8), Cardiovascular Effects of commonly Used Ophthalmic Medications.

Wand et al. Thymoxamine hydrochloride: an alpha-adrenergic blocker, Surv Ophthalmol. Sep.-Oct. 1980;25(2), printed from http://www.ncbi.nlm.nih.gov/pubmed/6108620, Abstract only, 1 page.

Zetterstrom, The effects of thymoxamine, phenylephrine and cyclopentolate on the accommodative process in man, Acta Ophthalmol (Copenh). Dec. 1987;65(6), printed from http://www.ncbi.nlm.nih.gov/pubmed/2963479, Abstract only, 2 pages.

Doughty et al., A review of the clinical pharmacokinetics of pilocarpine, moxisylyte (thymoxamine), and dapiprazole in the reversal of diagnostic pupillary dilation, Optom Vis Sci. May 1992; 69(5), printedfromhttp://www.ncbi.nlm.nih.gov/pubmed/1350669, Abstract only, 1 page.

Molinari et al., Dapiprazole's effect upon accommodative recovery: it is due entirely to changes in depth of field?, Optom VisSci. Aug. 1995;72(8), printed from http://www.ncbi.nlm.nih.gov/pubmed/8539022, Abstract only, 2 pages.

Orna Geyer, et al., "The Additive Miotic Etttects of Dapiprazole and Pilocarpine", Nov. 3, 1994, pp. 448-451.

Leonardo Mastropasqua, et al., "The Usefulness of Dapiprazole an Alpha-Adrenergic Blocking Agent, in Pigmentary Glaucoma", Oct. 4, 1994, pp. 806-809.

R. Mapstone, "Closed-angle glaucoma. Experimental results", St. Paul's Eye Hospital, Jun. 6, 1973 pp. 41-45.

Michael J. Doughty et al., "A Review of the Clinical Pharmacokinetics of Pilocarpine, Moxisylyte (Thymoxamine), and Dapiprazole in the Reversal of Diagnostic Pupillary Dilation", Optometry and Vision Science, vol. 69, Nov. 5, 1992, pp. 358-362.

David H. Abramson, et al., "Pilocarpine in the Presbyope", Demonstration of an Effect on the Anterior Chamber and Lens Thickness, Arch Ophthalmol/vol. 89, Feb. 1973, pp. 100-102.

Bernard Gilmartin, et al., "Reversal of Tropicamide Mydriasis with Single Instillations of Pilocarpine can Induce Substantial Pseudomyopia in Young Adults", Ophthal. Physiol. Opt. vol. 15, Nov. 5, 1995, pp. 475-479.

Alan I. Mandell, et al., "Reduced Cyclic Myopia with Pilocarpine Gel", Annals of Ophthalmology, vol. 20, 1988, pp. 133-135.

Nicola Iugliio, "Ocular Effects of Topical Application of Dapiprazole in Man", Glaucoma, May-Jun. 1984, pp. 110-116.

\* cited by examiner

OPTICAL CORRECTION

CROSS-REFERENCE TO RELATED APPLICATION

The present application claims the benefit of and priority to U.S. patent application Ser. No. 13/692,257 filed on Dec. 3, 2012, now U.S. Pat. No. 8,829,037, which claims the benefit of and priority to U.S. patent application Ser. No. 12/334,916 filed on Dec. 15, 2008, abandoned, which claims the benefit of and priority to British Patent Application No. 0724558.2, filed in the United Kingdom on Dec. 15, 2007, the entire disclosures of which are incorporated herein by reference.

BACKGROUND

1. Technical Field

The present invention relates to topical compositions to improve visual acuity and to methods for their use. More particularly, but not exclusively, it relates to eye-drops and the like to ameliorate the effects of presbyopia, myopia, hypermetropia, astigmatism and combinations thereof 2. Background of Related Art One prevalent form of visual defect is presbyopia, in which the lens of the eye becomes relatively rigid, particularly with age, so that it becomes increasingly difficult to focus. This leads to eyestrain, and ultimately to recession of the near point, such that a sufferer of presbyopia may be unable to read or work on objects at arm's length.

The conventional response to presbyopia is the use of reading glasses of appropriate strength to move the wearer's near point sufficiently close to allow clear vision at convenient reading and working distances. However, since this will probably also move the wearer's far point closer, sacrificing their distance vision, reading glasses must usually be removed for driving, for example.

Alternatively or additionally, reading glasses are produced whose lenses cover only a small portion of the visual field, so that the wearer may look round them for distance vision. However, the field covered by the lenses may not be sufficient for all purposes.

Bifocal spectacles comprise lenses having zones of different curvatures (or refractive indices), one zone producing a close-in near point for reading, etc, and the other producing a far point at or near infinity for distance work. Varifocal lenses are similar, but with the zones graduating into one another, rather than having a sharp division. Again, the restricted field covered by the "reading" portion of the lens may not be satisfactory, and many people cannot get used to bifocal lenses. Bifocal lenses are usually more expensive than standard lenses.

Furthermore, many people dislike wearing any form of spectacles for reasons of comfort or for reasons of personal style. Contact lenses have been proposed that are akin to bifocal spectacle lenses, but many people are uncomfortable with wearing contact lenses.

Surgical interventions include laser surgery to change corneal curvature, and intraocular implants. Many sufferers from presbyopia would not be prepared to risk (or pay for) corrective surgery.

There are thus drawbacks with each of the known approaches for improving a presbyope's ability to see nearby objects.

Myopia is a visual defect in which the cornea is too steeply curved, or the eyeball is too long, for light from significant distances to be focused on the retina, irrespective of the performance of the lens. A sufferer from myopia thus has a far point closer than infinity, conventionally known as "short sight". The converse defect is hyperopia or hypermetropia, in which the cornea is too flat, or the eyeball too short, for light from nearby objects to be focused on the retina (again, irrespective of the condition of the eye lens). This leads to a near point a significant distance from the eye, and similar problems to those resulting from presbyopia.

Myopia and hypermetropia may be corrected with spectacles or contact lenses of appropriate curvature, or by surgical intervention, akin to the approaches described above in respect of presbyopia. However, the same drawbacks are also experienced.

Similar drawbacks are found in existing approaches to correcting various other minor refractive errors of the eye. A further complication is that it is not uncommon to suffer from more than one vision defect; for example, a degree of astigmatism is often present for myopes and hypermetropes.

It is hence an object of the present invention to provide a means for improving close-in vision for those suffering from presbyopia or hypermetropia, and/or for improving distance vision for those suffering from myopia, that is simple, convenient and comfortable to use and which obviates the disadvantages of existing approaches. It is also an object of the present invention to provide a means for ameliorating refractive errors of the eye that has the same benefits and/or obviates the same disadvantages. It is a preferred object of the present invention to provide a means of addressing multiple vision problems at once. It is a further object of the present invention to provide a method for ameliorating the effects of presbyopia, myopia, hypermetropia and/or refractive error.

SUMMARY

The present disclosure describes a medicament for topical administration to a human or animal eye. The medicament includes a first active agent which contains a parasympathetic agonist, and a second active agent selected from the group consisting of a sympathetic antagonist, a sympathetic agonist and combinations thereof.

In addition, the present disclosure describes methods for improving visual acuity and also methods for treating a variety of eye disorders. Some non-limiting examples of the eye disorders include presbyopia, myopia, hypermetropia, astigmatism, and combinations thereof.

In embodiments, a method for improving visual acuity is disclosed which includes administering a first active agent containing a parasympathetic agonist to an eye, and then administering a second active agent selected from the group consisting of a sympathetic antagonist, a sympathetic agonist, and combinations thereof.

In embodiments, a method of improving visual acuity includes administering a single composition comprising a first active agent and a second active agent to an eye, wherein the first and second active agents are selected from the group consisting of a parasympathetic agonist, sympathetic antagonist, a sympathetic agonist, and combinations thereof. In some embodiments, the first active agent contains a parasympathetic agonist.

In other embodiments, a method for treating an eye disorder is disclosed which includes administering a first active agent containing a parasympathetic agonist to an eye, and then administering a second active agent selected from the group consisting of a sympathetic antagonist, a sympathetic agonist, and combinations thereof.

In still other embodiments, a method for treating an eye disorder is disclosed which includes administering a single composition comprising a first active agent and a second active agent to an eye, wherein the first and second active agents are selected from the group consisting of a parasympathetic agonist, sympathetic antagonist, a sympathetic agonist, and combinations thereof. In some embodiments, the first active agent contains a parasympathetic agonist.

DETAILED DESCRIPTION

According to a first aspect of the present disclosure, there is provided a medicament adapted for topical administration to a human or animal eye, comprising at least two pharmacologically active agents, a first said active agent comprising a parasympathetic agonist, and a second said active agent comprising either a sympathetic antagonist or a sympathetic agonist.

In embodiments, the medicament comprises a liquid composition.

Advantageously, the medicament comprises a liquid composition applicable to the eye in drop form.

Alternatively, the medicament may comprise a gel or ointment.

The medicament may comprise a slow release composition, optionally comprising slow release insert means.

In embodiments, said parasympathetic agonist comprises a substance adapted to act on acetylcholine receptors.

Advantageously, said parasympathetic agonist comprises pilocarpine.

The medicament may then comprise between 0.05% and 4% pilocarpine, optionally at least 0.25% and optionally no more than approximately 0.5%.

Preferably, the second active agent comprises a sympathetic antagonist adapted to act as an α-receptor blocker.

The sympathetic antagonist may advantageously comprise dapiprazole.

The medicament may then comprise between 0.05% and 4% dapiprazole, optionally at least 0.25% and optionally no more than approximately 0.5%.

The sympathetic antagonist may comprise thymoxamine.

The medicament may then comprise between 0.05% and 4% thymoxamine, optionally at least 0.25% and optionally no more than approximately 0.5%.

The sympathetic antagonist may comprise a β-blocker.

Alternatively, the second active agent may comprise a sympathetic agonist.

The sympathetic agonist may comprise brimonidine.

The medicament may then comprise between 0.01% and 4% brimonidine, and optionally at least about 0.1% thereof.

The sympathetic agonist may comprise iopidine.

The medicament may comprise at least one further component adapted to reduce discomfort of an eye treated with the medicament.

According to a second aspect of the present invention, there is provided a use of a combination of a first pharmacologically active agent comprising a parasympathetic agonist and a second pharmacologically active agent comprising a sympathetic antagonist or a sympathetic agonist in the manufacture of a medicament adapted for topical application to a human or animal eye in order to improve visual acuity.

Said medicament may be adapted to treat presbyopia.
Said medicament may be adapted to treat myopia.
Said medicament may be adapted to treat hypermetropia.
Said medicament may be adapted to improve night or low-light vision.

Said medicament may be adapted to treat defects of visual acuity such as astigmatism.

Said medicament may be adapted to treat more than one of the above conditions simultaneously.

According to a third aspect of the present invention, there is provided a method for improving visual acuity comprising the step of administering to an eye a combination of a first pharmacologically active agent comprising a parasympathetic agonist and a second pharmacologically active agent comprising a sympathetic antagonist or a sympathetic agonist.

Preferably, the method comprises the steps of providing a single composition comprising each of said first and second active agents, and administering said composition to the eye.

Alternatively, the method comprises the steps of administering sequentially to the eye respective compositions containing said first and second active agents.

Embodiments of the present invention will now be more particularly described by way of example.

An otherwise conventional eye-drop formulation was prepared, into which was incorporated 0.5% by weight dapiprazole and 0.5% by weight pilocarpine, to produce a first eye-drop formulation embodying the present invention. Dapiprazole is classified as a sympathetic antagonist; pilocarpine as a parasympathetic agonist.

In a first example, a patient aged sixty-three presented as an emmetrope (not requiring glasses for functional distance vision). The patient's vision was tested, the first eye-drop formulation was administered, and the patient's vision was then re-tested. Within twenty months of administration, the patient's unaided distance vision in each eye had improved by a line on the Snellen chart, from 6/6 to 6/5. The refraction did not change. The patient's unaided reading vision improved from N12 to N4.5 at a reading distance of one third of a meter. The patient's night vision improved qualitatively, as the patient noted less haloes and glare, and quantitatively, from 6/6 to 6/5 in dim conditions. These effects were maintained for two hours and some for at least four hours.

The first eye-drop formulation thus improves both near and distance vision. In a second example, a patient aged fifty presented as a −4 Dioptre myope (requiring glasses for functional distance vision). Again, the patient's vision was tested before and after the first eye-drop formulation was administered. Within half an hour of administration, the patient's unaided distance vision improved from being able to count fingers (but not to read the Snellen chart) to 6/36 on the chart. Wearing distance-corrected glasses, the patient's reading vision at a distance of one third of a meter improved from N12 to N4.5. The refraction did not change. Quality of night vision improved as the patient noted less haloes and glare, and night vision also improved quantitatively from 6/6 to 6/5 in dim conditions. The effects again were maintained for two hours and some for at least four hours.

In a third example, a patient aged forty-nine presented as a +4 Dioptre hypermetrope (longsighted and requiring glasses for useful reading vision). The patient's vision was tested before and after administration of the first eye-drop formulation. Within half an hour of administration, the patient's unaided distance vision improved on the Snellen chart from 6/60 to 6/24. The patient's unaided reading vision at one third of a meter improved from N18 to N4.5. The refraction did not change. Quality of night vision improved, the patient noting less haloes and glare, and night vision also improved quantitatively from 6/6 to 6/5 in dim conditions. The effects were maintained for two hours and some for at least four hours.

In all three examples, no significant discomfort was reported.

A second eye-drop formulation embodying the present invention was prepared by incorporating 0.1% by weight brimonidine and 0.25% by weight pilocarpine into an otherwise conventional eye-drop formulation. Brimonidine is classified as a sympathetic agonist: pilocarpine, as noted above, is considered to be a parasympathetic agonist.

The second eye-drop formulation was tested on the three patients referred to above. In each case, administration of the second eye-drop formulation produced almost identical effects to the first eye-drop formulation, above.

A third and fourth eye-drop formulation were made up, containing 0.5% dapiprazole and 0.5% pilocarpine, respectively. Administration of the third and fourth eye-drop formulations immediately sequentially to a patient's eyes produced results substantially identical to those from the first eye-drop formulation (which contained the same active components, pre-mixed). Thus, the eye-drop formulations of the present invention may in effect be produced in situ in the patient's eye, should this be convenient. (NB: the effects of the third or fourth eye-drop formulations administered alone would be substantially inferior to those of the first formulation, or to those of the third and fourth formulations, either mixed before administration or in the eye).

There are signs that the eye-drop formulations of the present invention also obviate the effects of astigmatism. Thus, they will be useful for the many patients who suffer from combinations of vision problems, such as myopia coupled with astigmatism. (Such effects make prescribing and producing appropriate spectacle lenses, or other conventional approaches, particularly difficult).

It is particularly notable from the above results that not only do the compositions of the present invention significantly improve the unaided distance vision of myopes and the unaided close-up vision of hypermetropes, but they also improve the clarity of close-up vision for myopes, distance vision for hypermetropes and vision both near and far for emmetropes. It is also evident from these results that presbyopes would also benefit from treatment with these compositions. Presbyopia usually takes the form of difficulty in focusing on nearby objects (accommodation). Compositions such as those of the present invention, which do not act by changing refraction, are thus likely to be more desirable and effective than those compositions that have occasionally been proposed in the past, which do change refraction. The effect on night vision haloes, etc, suggests that other form of refractive error might also be ameliorated.

The eye-drops of the present invention may thus be used temporarily to alleviate the effects of conditions such as myopia and hypermetropia or to improve adequate vision further. It is envisaged that, due to the lack of side-effects and drawbacks discovered in testing to date, these eye-drops might well be suitable for self-selection and self-administration, rather than needing to be prescribed by a qualified medical practitioner.

Thus, the eye-drops of the present invention could be used in place of corrective glasses or contact lenses, either as a general practice: for variety; or in particular circumstances where glasses and/or contact lenses might not be practical or convenient (e.g. contact sports).

The exact physiological mode of action of these combinations of pharmaceuticals has not yet been established. The most significant and unexpected feature of their action appears to be that combining parasympathetic agonists and sympathetic antagonists, agents having largely opposite modes of action, produces beneficial synergies relative to either agent used separately, while their possible adverse effects appear largely to cancel out.

It is also most unexpected that parasympathetic agonists and sympathetic agonists appear to co-operate synergistically, without significant side-effects.

It is believed that at least part of the benefit of the combinations described is because they seem to have little or no net effect on the ciliary muscles of the eye, which act to alter the shape and hence refraction of the lens.

While the examples above describe application in the form of eye-drops, other forms of topical application to the eye may be possible. There is no reason to believe that spraying compositions with the same combinations of active agents into the eye; applying a gel or ointment to the eye; or even using an ocular insert containing a slow-release preparation of one of the above combination of active agents would not work similarly well.

It is possible that certain otherwise suitable active agents might lead to issues with general discomfort in the eye, or even specific side-effects such as red-eye, in which blood vessels of the sclera dilate so far that some or all of the white of the eye appears red. The treatment could be completed with separate administration of further compositions selected on a symptomatic basis. However, it is probably more convenient to incorporate the appropriate treatment agents into the compositions of the present invention, particularly where the side-effect is frequently encountered.

As well as the active agents exemplified above, others that are believed to be particularly suitable for the compositions of the present invention include: thymoxamine, a sympathetic antagonist (substitutable for dapiprazole); and iopidine, a sympathetic agonist (substitutable for brimonidine). The class of drugs generally referred to as beta-blockers may be considered as sympathetic antagonists, and hence some or all of that class may well be usable in place of dapiprazole, above.

It is also believed that an opiate could be substituted for either the parasympathetic agonist or the sympathetic antagonist/agonist in the compositions above. Indeed, a composition containing an opiate as its sole or main active component is predicted to be effective in the treatment of the conditions listed above.

What is claimed is:

1. A method for treating an eye disorder without the use of a contact lens comprising:
    administering a first eye-drop formulation including pilocarpine to an eye suffering from the eye disorder, and
    administering a second eye-drop formulation including dapiprazole wherein the eye disorder is an astigmatism.

2. The method of claim 1 further treating a second eye disorder selected from the group consisting of presbyopia and myopia.

3. A method for treating an eye disorder without the use of a contact lens comprising:
    administering a single eye-drop formulation to an eye suffering from the eye disorder, the eye-drop formulation including dapiprazole and pilocarpine, wherein the eye disorder is an astigmatism.

4. The method of claim 3 further treating a second eye disorder selected from the group consisting of presbyopia and myopia.

5. The method of claim 3 wherein the dapiprazole is from about 0.05 to about 4%.

6. A method for treating a combination of eye disorders without the use of a contact lens comprising:
    administering a single eye-drop formulation to an eye suffering from a combination of eye disorders, the eye-drop formulation including pilocarpine and about 0.05 to about 4% dapiprazole, wherein the combination of eye disorders includes an astigmatism and a second eye disorder selected from the group consisting of presbyopia and myopia.

7. The method of claim 6 wherein the second eye disorder is myopia.

8. The method of claim 6 wherein the second eye disorder is presbyopia.

9. The method of claim 6 wherein administering the single eye-drop formulation to the eye suffering from the combination of eye disorders does not change refraction of a lens of the eye.

10. The method of claim 9 wherein the pilocarpine is from about 0.05 to about 4%.

11. The method of claim 1 wherein the dapiprazole is from about 0.05 to about 4%.

12. The method of claim 11 wherein the pilocarpine is from about 0.05 to about 4%.

13. The method of claim 12 wherein administering the second eye-drop formulation to the eye suffering from the eye disorder does not change refraction of a lens of the eye.

14. The method of claim 5 wherein the pilocarpine is from about 0.05 to about 4%.

15. The method of claim 14 wherein administering the single eye-drop formulation to the eye suffering from the eye disorder does not change refraction of a lens of the eye.

\* \* \* \* \*